United States Patent
Derakhshan

(10) Patent No.: US 6,516,246 B2
(45) Date of Patent: Feb. 4, 2003

(54) METHOD AND SYSTEM FOR DETERMINING NATIVE NEUROLOGICAL DOMINANT HEMISPHERE

(75) Inventor: Iraj Derakhshan, Charleston, WV (US)

(73) Assignee: Mimicking Man Manually, Inc., Charleston, WV (US)

( * ) Notice: Subject to any disclaimer, the term of this patent is extended or adjusted under 35 U.S.C. 154(b) by 0 days.

(21) Appl. No.: 09/948,788

(22) Filed: Sep. 10, 2001

(65) Prior Publication Data

US 2002/0065580 A1 May 30, 2002

Related U.S. Application Data

(60) Provisional application No. 60/231,707, filed on Sep. 11, 2000, provisional application No. 60/263,184, filed on Jan. 23, 2001, provisional application No. 60/283,644, filed on Apr. 16, 2001, provisional application No. 60/298,078, filed on Jun. 15, 2001, and provisional application No. 60/303,596, filed on Jul. 6, 2001.

(51) Int. Cl.$^7$ .............................................. G06F 19/00
(52) U.S. Cl. .................... 700/245; 700/257; 424/199.1; 424/205.1; 424/229.1; 600/409; 600/544; 600/545; 701/23; 324/248
(58) Field of Search ................................ 700/245, 257; 424/205.1, 186.1, 231, 1; 701/23, 199.1, 229.1; 600/544, 545, 409; 435/235.1, 236, 9.1, 317.1, 455; 324/248; 349/11

(56) References Cited

U.S. PATENT DOCUMENTS

| | | | | |
|---|---|---|---|---|
| 4,859,587 A | * | 8/1989 | Roizman | 424/199.1 |
| 5,713,354 A | * | 2/1998 | Warden | 600/409 |
| 5,840,040 A | * | 11/1998 | Altschuler et al. | 600/544 |
| 5,853,733 A | * | 12/1998 | Cochran et al. | 424/199.1 |
| 5,928,648 A | * | 7/1999 | Cochran | 424/199.1 |
| 5,961,982 A | * | 10/1999 | Cochran | 424/199.1 |
| 5,965,138 A | * | 10/1999 | Cochran et al. | 424/199.1 |
| 6,120,773 A | * | 9/2000 | Roizman | 424/186.1 |
| 6,169,981 B1 | | 1/2001 | Werbos | |
| 6,171,239 B1 | | 1/2001 | Humphrey | |
| 6,183,753 B1 | * | 2/2001 | Cochran et al. | 424/199.1 |

OTHER PUBLICATIONS

Johan Wessberg et al., "Real–time prediction of hand trajectory by ensembles of cortical neurons in primates", Nature, vol. 408, Nov. 16, 2000, pp. 361–365.

John K. Chapin et al, "Real–time control of a robot arm using simultaneously recorded neurons in the motor cortex", Nature Neuroscience, vol. 2, No. 7, Jul. 1999, pp. 664–670.

Jerome N. Sanes, "The Relation Between Human Brain Activity and Hand Movements", NeuroImage 11, 2000, pp. 370–374.

(List continued on next page.)

Primary Examiner—William A. Cuchlinski, Jr.
Assistant Examiner—M McDieunel Marc
(74) Attorney, Agent, or Firm—Connolly Bove Lodge & Hutz LLP

(57) ABSTRACT

A method and system for determining the dominant cerebral hemisphere of a subject. There is further provided a method and system for using information obtained regarding hemisphere dominance for programming electronic devices such as robots, prostheses, as well as methods for using such information during treatment and surgical procedures in order to obtain superior function and/or movement when there is injury or disease to an area of the brain. A vectorial view of the role of callosum in the underpinning lateralities of speech and handedness, and as such, provides a technical definition of handedness (i.e., which hemisphere of the cerebrum is dominant in a particular individual subject). This technical definition is then used to completely accurately replicate or predict voluntary movements of the subject and this information, in turn, can be utilized in the field of prosthetics and robotics in order to obtain more accurate depiction of brain function and hence, more authentic replication of movement.

13 Claims, 1 Drawing Sheet

OTHER PUBLICATIONS

"A spelling device for the paralysed", Nature, Mar. 25, 1999, pp. 297–298.

Bagrat Amirikian et al, "Cortical Populations and Behaviour: Hebb's Thread", Canadian Journal of Experimental Psychology, 1999, 53:1, pp 21–34.

"Neuronal Coding and Robotics", Science, vol. 237, No. 4812, Jul. 17, 1987, pp 300–301.

Carlo A. Marzi, "The Poffenberger paradigm: A first, simple behavioural tool to study interhemispheric transmission in humans", Brain Research Bulletin, vol. 50, Nos. 5/6, 1999, pp. 421–422.

D. Chawla et al., "The physiological basis of attentional modulatino in extrastriate visual areas", Nature Neuroscience, vol. 2, No. 7, Jul. 1999.

Chapin, et al, J Neurosci Methods, Dec. 15, 1999, Pub Med abstract relating to "Principal component analysis of neuronal ensemble activity reveals multidimensional somatosensory representations", 2 pages.

Nicolelis et al, J Neurophysiol Sep. 1997, Pub Med abstract relating to "Neonatal whisker removal reduces the discrimination of tactile stimuli by thalamic ensembles in adult rats", 2 pages.

Chapin, Curr Opin Neurol Dec. 2000, Pub Med abstract relating to "Neural prosthetic devices for quadriplegia", 1 page.

Chapin, Prog Brain Res, 2000, Pub Med abstract relating to "Impact of neuroprosthetic applications on functional recovery", 1 page.

Nicolelis et al, Science Jun. 2, 1995, Pub Med abstract relating to "Sensorimotor encoding by synchronous neural ensemble activity at multiple levels of the somatosensory system", 1 page.

Chapin, Electroencephalogr Clin Neurophysiol Suppl 1996, Pub Med abstract relating to "Neural network mechanisms of oscillatory brain states: characterization using simultaneous multi–single neuron recordings", 1 pg.

Nicolelis et al., J Neurophysiol 1996, Pub Med abstract relating to "Active tacile exploration influences the functional maturation of the somatonsensory system" 2 pages.

Nicolelis et al., Nat Neurosci, Nov. 1998, Pub Med abstract relating to "Simulaneous encoding of tactile information by three primate cortical areas", 1 page.

Zeck et al., Proc Natl Acad Si USA Aug. 28, 2001, abstract relating to "Noninvasive neuroelectronic interfacing with synaptically connected snail neurons immobilized on a semiconductor chip".

Iacoboni et al., Parallel visuomotor processing in teh split brain: Cortico–subcortical interactions, 2000, Internet, pp. 759–769.*

DiCarlo et al., Structure of receptive fields in area 3b of primary somatosensory cortex in the alert monkey, 1998, Internet, pp. 2626–2645.*

Ackerman et al., Hemispheric lateralization of teh neural eecoding of the temporal speech features: a whole–head magnetencephalography study. no date, Internet, p. 1.*

* cited by examiner

METHOD AND SYSTEM FOR DETERMINING NATIVE NEUROLOGICAL DOMINANT HEMISPHERE

PRIORITY CLAIM

The present application claims priority to provisional applications Serial No. 60/231,707, filed Sep. 11, 2000; Serial No. 60,263,184, filed Jan. 23, 2001; Serial No. 60/283,644, filed Apr. 16, 2001; Serial No. 60/298,078, filed Jun. 15, 2001; and Serial No. 60/303,596, filed Jul. 6, 2001, the content of which are each incorporated herein by reference in their entireties.

BACKGROUND OF THE INVENTION

1. Field of the Invention

The present invention relates generally to methods for determining the dominant cerebral hemisphere of a subject and in particular, to novel methods and systems for recognizing and implementing a subject's dominant hemisphere for therapeutic and other uses.

2. Description of the Related Art

Understanding how a primate or human brain functions in making decisions and implementing voluntary and involuntary movements has been studied and analyzed for many years. At one time, there was a theory that there is contralaterality of motor control in humans. However, substantial clinical evidence suggests that the contralaterality theory is problematic. Thus, during surgical procedures and other therapeutic treatments involving the brain, errors in judgment in terms of which lobe of the cerebrum controls which movements can be made by the attending physician since a person's actual "wiring" for either left or right handedness might have been reversed by environmental factors, but the fact remains that their actual dominant hemisphere is as genetically predisposed.

That around 90% of the population is right handed and the remainder is not, is an agreed upon statistic. Yet there is no technical definition of handedness, only arbitrary inventories. But even those have been disputed on several grounds, including that a person's stated manual preference does not always, or even often, match their observed performance; taking us back to where we started. Clearly a technical definition of handedness is needed to escape from the dilemma thus posed as well as a development of an understanding of the neural underpinning of the prior observations is needed in the art. Such an understanding provides the framework for software to be programmed in the control of robotics or prosthesis, and additionally will be useful to surgeons during procedures when it is highly advantageous to know for a certainty which cerebral hemisphere of the subject being treated is dominant.

SUMMARY OF THE INVENTION

In accordance with the present invention, there is provided a method and system for determining the dominant cerebral hemisphere of a subject. There is further provided a method and system for using information obtained regarding hemisphere dominance for programming electronic devices such as robots, prostheses, as well as methods for using such information during treatment and surgical procedures in order to obtain superior function and/or movement when there is injury or disease to an area of the brain. The present invention employs a vectorial view of the role of callosum in the underpinning lateralities of speech and handedness, and as such, provides a technical definition of handedness (i.e., which hemisphere of the cerebrum is dominant in a particular individual subject). This technical definition is then used to completely accurately replicate or predict voluntary and involuntary movements of the subject and this information, in turn, can be utilized in the field of prosthetics and robotics in order to obtain more accurate depiction of brain function and hence, more authentic replication of movement.

Additional objects, features and advantages of the invention will be set forth in the description which follows, and in part, will be obvious from the description, or may be learned by practice of the invention. The objects, features and advantages of the invention may be realized and obtained by means of the instrumentalities and combination particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENT

Figure 1:
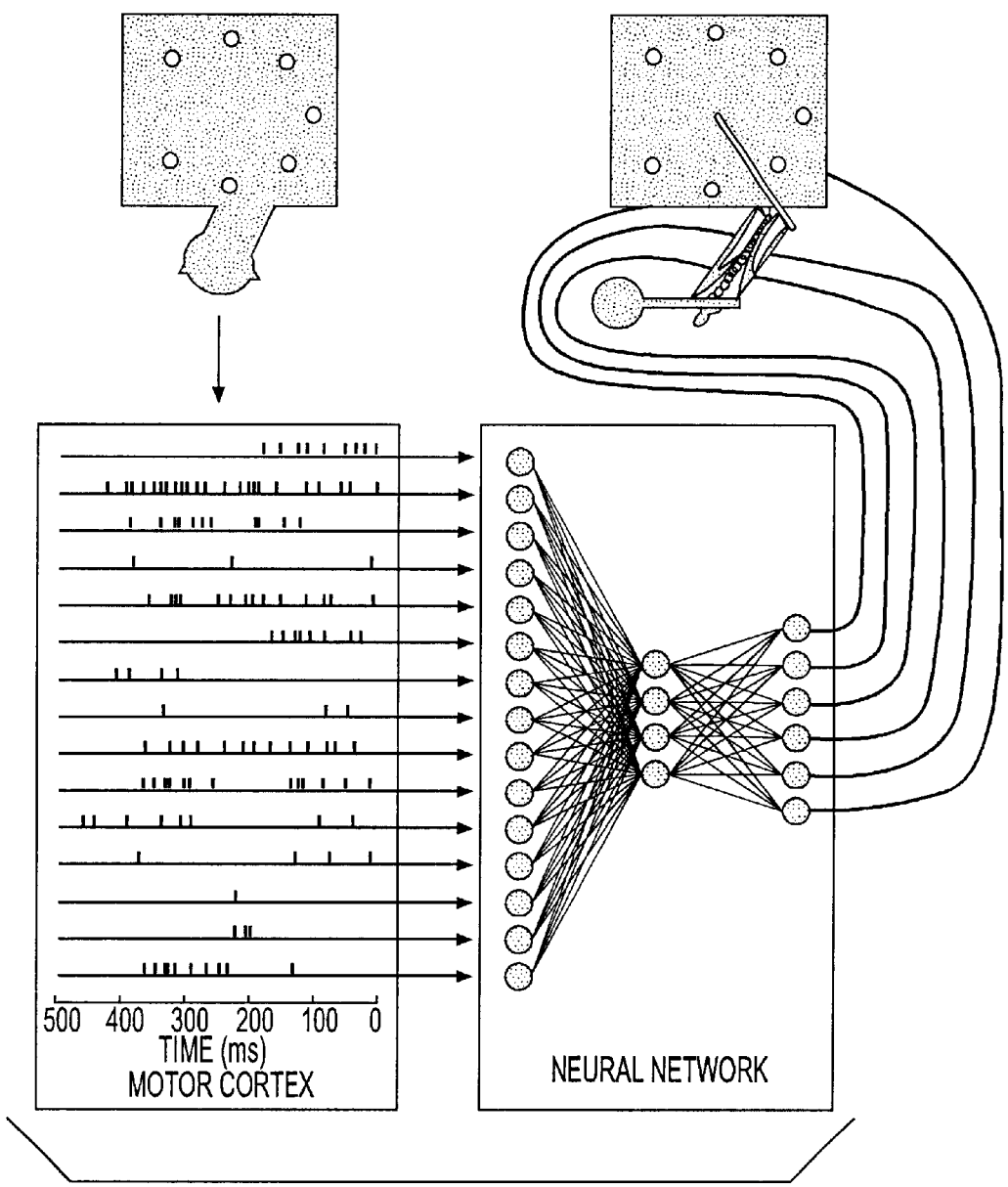
FIG. 1 illustrates how signals recorded from a human subject's motor cortex are translated into an artificial neural network to control a robotic arm according to the present invention.

In accordance with the present invention, inter alia, there is provided an explanation for the enigmas of crossed aphasia and crossed nonaphasia: Crossed aphasia is present when the manifest handedness of a subject demands its absence, while crossed nonaphasia denotes absence of aphasia when the manifest handedness of subject demands its presence. The vectorial theory exposed herein is based in large part upon the existence a "devoted neuronal aggregate" (referred to herein as "DNA") for executive functions (i.e. speech and handedness) amalgamated within the motor apparatus of each hemisphere with its major moiety in the dominant hemisphere and the minor moiety in the minor hemisphere, mediating bimanual coordination via the callosum. It is the major moiety however that forms a person's "real neurological address" (referred to herein as "RNA"), wherein a person's neurological identity lies. The DNA is considered as one entity, the division of which is occasioned by the existence of a gap (i.e. callosum) between its two moieties. Thus it is the housing of the major moiety of the DNA within the left hemisphere of the vast majority of people that make them left hemisphere dominant for speech and right handed for dexterity. The situation is the reverse for left handed subjects. The dominant hemisphere can be found using tests according to the Poffenberger paradigm such as disclosed in Marzi, "The Poffenberger Paradigm: A first, simple behavioural tool to study interhemispheric transmission in humans," Brain Research Bulletin, Vol. 50 Nos. 5/6 pp. 421–422 (1999), the content of which is incorporated herein by reference in its entirety. In addition, the dominant hemisphere can be found utilizing Positron Emission Tomography Scanning ["PET"], Functional Magnetic Resonance Imaging ["FMRI"], Transcranial Magnetic Stimulation ["TMS"] or according to Poffenberger's Method. All of these methods are well known in the art. What was not known, however, before the present invention, was that crossed aphasia and crossed nonaphasia find their solution in employing a vectorial view of analysis. Namely, the classical theory assumed complete isolation of each hemisphere when performing tasks involving iseomotor sites located within the same hemisphere. The vectorial view of the present invention, on the other hand, provides that all voluntary movements begin from the dominant hemisphere regardless of which hand is used to perform a task. Namely, there exists a devoted neuronal aggregate for executive functions (i.e. speech and handedness) amalgamated within the motor apparatus of each hemisphere with its major moiety in the dominant hemisphere and the minor moiety in the minor hemisphere, mediating bimanual coordination via the callosum. The major moiety forms a person's real neurological address (RNA), wherein a persons neurological identity lies. The DNA as one entity, and is divided by a gap (i.e. callosum) between its two moieties. Since most people are left hemisphere dominant, the major moiety of the DNA within the left hemisphere of their brains makes them left hemisphere dominant for speech and right handed for dexterity. The situation is the reversed for left handers. According to the vectorial view of the present invention, there is an executor located at one or the other hemisphere, depending on a person's real neurological identity (RNA). Since all volitional activities begin from the DNA with the bulk of it located in the major hemisphere (usually the left) the left hand follows the lead of the right hand by an amount equal to the interhemispheric transfer time (IHTT). And since this allows for the right hand to volunteer first and do more of daily activities it becomes the preferred hand. As the two DNA moieties are part and parcel of the same substrate, an involvement of the major moiety is associated with bilateral manifestation of the effect of that lesion while the involvement of the minor moiety, or the liaison between the two moieties, will manifest itself only at one side; i.e. contralaterally. Transhemispheric diaschisis and the facilitating nature of the neuronal connection between the moieties of the DNA indicates that there should be circumstances in which manifestation of deafferentation of the minor hemisphere is seen ipsilateral to a lesion with or without the presence of an excitatory phenomenon on the opposite side of the body. Table 1–3 attached hereto are products of an exhaustive review of literature in support of vectorial view's assumptions/predictions, as seen at the bedside.

In accordance with the present invention, principles similar or identical to those described in Amirikian et al., "Cortical Populations and Behavior: Hebb's Thread" *Canadian Journal of Experimental Psychology,* pp. 21–34 (1999) (the content of which is incorporated herein by reference), are used to create an artificial neural network to drive a prosthesis, a robot, and/or to create a map of how brain signals translate to movement. In the artificial neural network of Amirikian, however, monkey brains are analyzed in connection with powering a robotic arm. Monkeys do not display handedness characteristics in the same manner as human beings (approximately 50% of monkeys are left handed and 50% are right handed), and as such, there is no relevance in a monkey's handedness in mapping its brain signals that determine movement. However, what has been found in accordance with the present invention is that the dominant hemisphere, the actual wiring of which lobe of the cerebrum dominates the handedness in a human being is very critical in simulating movement that is realistic. That is, movement is tied very greatly to which hemisphere of the brain is dominant. Thus, if one wants to replicate accurately the way a human being conducts movements and limbs cooperate to accomplish tasks such as walking, lifting items, etc., then the instant inventor has found that one must first make a determination of the dominant hemisphere of the subject and modify the formation of the artificial neural network accordingly.

In this regard, it is known from Amirikian that changes in the motor cortical cell activity precedes the development of the motor output and relates quantitatively to its intensity and spatial characteristics. Specifically, when reaching in space, cell activity during the reaction time relates primarily to the direction of the movement and less to its extent. Cell activity is highest for a movement in a particular direction and decreases progressively with movements farther and farther away from this direction. The changes in cell activity relate to the direction and not the endpoint of the reaching movement. Quantitatively, the crucial variable on which cell activity depends is the angel formed between the direction of the movement and the cell's preferred direction: The intensity of the cell activity is a linear function of the cosine of this angle. Amirikian employs a vectorial neural calculation where a preferred vector represents the contribution of a directionally tuned cell and points in the cell's preferred direction; cell vectors are weighed by the change in cell activity during a particular movement; and the sum of these vectors (i.e., the population vector) provides the unique outcome of the ensemble coding operation. See Amirikian, p. 21–22 and FIG. 1 thereof.

The present invention takes the theory of Amirikian one step further by implementing a vectorial neural code wherein first a determination of the true dominant hemisphere of the human subject being analyzed is made. Then a vectorial map is prepared using computerized techniques similar to those described, for example, in U.S. Pat. Nos. 6,171,239 and 6,169,981, the contents of which are incorporated herein by reference in their entireties. In addition, devices and methods can be adapted for use with the present invention such as those described in Wessburg et al., "Real-time prediction of hand trajectory by ensembles of cortical neurons in primates" Nature. Nov. 16, 2000;408(6810):361-5, PMID: 11099043; Chapin J K, Moxon K A, Markowitz R S, Nicolelis M A. "Real Time control of a robot arm using simultaneously recorded neurons in the motor cortex". Nat Neurosci. Jul. 2, 1999;(7):664–70. PMID: 10404201 Amirikian B, Georgopoulos A P, Georggpulos A P., "Directional tuning profiles of motor cortical cells" Neurosci Res. January 2000;36(1):73-9. PMID: 10678534; Amirikian B, Georgopoulos A P. "Cortical populations and behaviour: Hebb's thread" Can J Exp Psychol. March 1999;53(1):21–34. Review. PMID: 10389487; Lukashin A V, Amirikian B R, Georgoipoulos A P. Related Articles "A simulated actuator driven by motor cortical signals." Neuroreport. Nov. 4, 1996;7(15–17):2597–601. PMID: 8981430, each of which is incorporated herein by reference in its entirety. Another method for transforming neuronal commands measured using the vectorial theory of the present invention can be made according to the model of present FIG. 1.

The top left part of FIG. 1 illustrates a human exerting a force against an immovable handle in one (180 degrees) of eight instructed directions. An example of the motor cortical activity recorded while the human performed this task is represented in the bottom left panel. The spike trains were recorded for different trials but for the same instructed direction of force. These neuronal signals drive the simulated actuator sketched in the top right part of the figure. The actuator muscles are modeled as nonlinear springs with an exponential length-tension relationship; $f(l)=k\{\exp[a(1-l")-1\}$ where f(l) is a contraction force developed by the muscle at length l, l" is the muscle rest length, and k and a are constants. A three-layered feedforward neural network (the directed connections are shown by thin arrows) transform cortical signals into coordinated activation of actuator muscles. Activities of units at the input layer are the spike trains taken as they are from an experimentally obtained data file. This data file is preprogrammed to compensate for the dominant hemisphere of the subject being evaluated based on the signal readings being recorded. The cortical activity converges in four model units located at the intermediate layer. The intermediate units provide integrated (over inputs and over time) signal to output units. Activities of intermediate and output units can be calculated, for example, using sigmoid activation function, $y(x)=\frac{1}{2}[1+\tan h(x-B)]$, where B is a threshold and x is a synaptic input entering into the unit. The output activity of the network changes the muscles rest lengths (each output unit innervates one muscle; a linear relation between the rest length l' and the output unit activity can be used: $l'(y)=a+by$, where a and b are constants). If the actuator is free to move, this will cause the contraction of muscles and, as a result, the actuator's endpoint will move into a new equilibrium position. If, however, the actuator's endpoint is blocked by an immovable object, then the tensions developed by muscles due to the change of the muscle rest lengths will produce the endpoint force against that object.

Interestingly, Amerikian states on page 27 that the mean rotation rate and the range of rates observed for different reference directions were very similar in his monkeys studied to those obtain in human studies. This is because monkeys do not display disparity of handedness. When the instant inventor attempted the Amerikian test on humans without any compensation for handedness, the coordination of the movement was not nearly as accurate as Amerikian found in primates. This is because unlike monkeys, the handedness of humans is very much related to the coordination of limbs during movement of the extremities.

Known methods for measuring brain electrical impulses are described, for example, in U.S. Pat. No. 4,862,359, the content of which is incorporated by reference in its entirety. Then the data obtained in the Poffenberger test is analyzed by applying a vectorial analysis comprising determining the handedness of the subject wherein negative crossed uncrossed differential (CUD) translate to a finding that all voluntary movements originate from the left hemisphere in true right handers (and the other way around in real left handers). Since there is no difference in signal detection between the two hemispheres, the temporal ranking order from signal to movement is employed to categorize such subject as VF/rh, uncrossed, and VF/lh, crossed in a right hand. The present method can be taken many steps further such as for controlling prosthetic and robotic devices as described, for example, in Sanes, "The Relation between Human Brain Activity and Hand Movements," *NeuroImage* 11, 370–374 (2000) (incorporated herein by reference in its entirety); for driving a muscle driven communication device as described in Birbaumer et al., *Nature*, Vol 398 pp. 297–298 (March 1999) (incorporated herein by reference in its entirety); using recorded NPs to control external movement devices Chawla et al., "The Physiological Basis of Attentional Modulation in Extrastriate Visual Areas," *Nature Neuroscience*, Vol. 2, No. 7 pp. 668–670 (July 1999) (incorporated herein by reference in its entirety), control robotics such as real time control of a robotic arm as described in Chapin et al., "Real Time Control of a Robot Arm Using Simultaneously Recorded Neurons in the Motor Cortex," *Nature Neuroscience*, Vol. 2, No. 7 pp. 664–668 (July 1999) (incorporated herein by reference in its entirety); and also use neural population signals for real time control of robotic devices, both locally and through the Internet as described in Wessberg et al., "Real Time Prediction of Hand Trajectory by Ensembles of Cortical Neurons in Primates," *Nature*, Vol. 408, pp. 361–365 (November 2000) (incorporated herein by reference in its entirety). In addition, certain functionalities could be provided according to the methods set forth in U.S. Pat. No. 6,169,981, the content of which is incorporated herein by reference in its entirety.

The present invention would permit a subject to control a device based on the subject's "intention" or based on "imagination." That is, the subject would imagine some action, and by measuring the brain waves according to known techniques and compensating for the dominant hemisphere origination of movement as disclosed herein, a prosthesis or robot could undertake the activity that is imagined or intended. According to the present invention, any intentional activity is known to originate from the dominant hemisphere. Therefore, according to methods and apparatus contemplated herein, robotics or prostheses would be controlled according to known techniques such as disclosed in U.S. Pat. No. 6,171,239, to Humphery entitle "Systems, Methods and Devices for Controlling External Devices By Signals Derived Directly From the Nervous System." Also, possible methodologies are disclosed by Amirikian et al. in "Cortical Populations and Behaviour: Hebb's Thread," *Canadian Journal of Experimental Psychology*, pp. 21–34 (1999), both of these documents are incorporated herein by reference in their entireties. However, while Humphrey employs many techniques that are similar to those espoused herein, the robotics or prostheses controlled according to the methodology of Humphrey will not be nearly as accurate in reproducing human coordination characteristics for the robot or prosthesis. This is because Humphrey in U.S. Pat. No. 6,171,239 does not include any compensation in his scheme for the dominant hemisphere of the cerebrum or how the handedness of the human subject who's brain signals are being used to control the external device.

The human brain is an exceedingly complex processing system, which integrates continual streams of incoming sensory input data with stored memories, uses the input data and memories in complex decision processes at both conscious and unconscious levels, and on the basis of these processes generates observable behaviors by activation of its motor or movement control pathways and the muscles which these innervate.

In certain cases of traumatic injury or neurological disease the brain is partially isolated from the periphery. Input data from certain senses are thus lost, at least for a portion of the body, as are many voluntary movements. Spinal cord injury is a well known example. With spinal cord injury, the pathways that link higher brain regions with the spinal cord and that are used for control of voluntary movements may be functionally transected at the site of injury. As a result, the patient is paralyzed, and (s)he can no longer voluntarily activate muscles that are innervated by regions of the spinal cord below the level of the injury. Despite the injury to their long fibers, however, many of the cells in these higher brain regions that control voluntary movement will survive and can still be activated voluntarily to generate electric signals for controlling voluntary movement. By recording directly from these cells with implantable devices (e.g., electrode arrays), signals generated by the cells may be "exteriorized" and used for the control of external prostheses, such as an assist robot or an artificial arm, or functional electrical stimulation paralyzed muscles. The brain signals measured according to the present invention include neuronal signals derived from a population of cells devoted to executive functions. These signals may be electrical or may be derived from the metabolic activity of these cells. Such measurements can be made, for example, by employing fMRI or PET scanning technologies. As such, according to the present technique, those signals that are derived from the cells devoted to executive function are the most important and are those that are screened or filtered to the device that has been programmed to compensate for the true handedness of the individual whose thought pattern or desired activity is sought to be mimiced.

Another example of such loss occurs in cases of amyotrophic lateral sclerosis (Lou Gebrig's Disease), in which the motor neurons which control muscles, as well as some of the brain cells that control these motor neurons, degenerate. In advanced stages of this disease, the patient may have completely intact senses and thought processes, but is "locked in", so that neither movements nor behavioral expressions of any kind can be made. Providing these patients with some way of communicating with the external world would greatly enhance their quality of life.

In sum, there is a need to develop a system for monitoring and processing the electrical signals from neurons within the central nervous system, so that the brain's electrical activity may be "exteriorized" and used for the voluntary control of external prostheses or assist devices. In this way, damaged pathways are circumvented and some control of the environment can be restored. Because the electrical fields of small groups of neurons drop off rapidly with distance from the cells, this system should include surgically implanted "tiny" electrodes or sensors, which can be placed in close proximity to the cells that generate command signals for voluntary movement.

In recent years, small, multichannel, micromachined (integrated circuit) electrodes have been developed for use in neural recording. A second approach is to use electrodes with larger exposed recording surfaces (in the range of 0.5 to 1.5 mm sq. surface area). These low impedance electrodes have lower noise characteristics than those with smaller tips, and can reliably record the activity of hundreds to thousands of neurons at greater distances than can the latter. Indeed, low level electroencephalographic (EEG) or field potentials can even be recorded from the surface of the scalp.

According to the present invention, any type of measurement device can be used to measure the electrical impulses coming from the brain. What is of utmost importance here is that there is first a determination of the dominant hemisphere of the subject using the techniques described herein. Then, when the electronic impulses are measured and inputted into the electronics that control the prosthesis or robot, there is a compensation for voluntary and involuntary movements to take into account the dominant hemisphere. That is, there is provided an algorithm that automatically determines which hemisphere is sending signals and determining whether a particular intention or imagination of the subject is voluntary or involuntary so that the appropriate action of the prosthesis or robot is accomplished with the highest degree of accuracy. The preferred method of present invention is capable of obtaining the neuronal signals that are specific to executive functions. These signals are then mapped and categorized to determine the actual dominant hemisphere. However, any methodology that employs a mechanism for neuroelectronic systems to be used for neuroprosthetics or the like would also be useful in the present invention. The systems described here are adaptable to a variety of signals from the brain or central nervous system as diverse as a) neurally generated electrical signals, recorded with microelectrode technologies from within the brain or with surface electrodes from extracranial sites; and/or (b) measures of localized blood flow that are correlated with neural activity, if techniques for miniaturization of current devices for making such measurements, in real time, are developed in the future. The external devices may include any device that can be controlled by processed electrical signals. These devices include, but are not limited to, artificial or prosthetic limbs; computer controlled, functional electrical stimulation of muscles of paralyzed individuals for the restoration of movement; robots or robotics components; computers or computer displays; or the teleoperation of robots and machines in hostile environments.

A preferred embodiment of the invention represents a unique blend of technologies from the fields of neuro- or electro-physiology, biomaterials science, neural signal processing, functional brain imaging (to guide implantation of sensors), and robotics or prosthetics. Included in the embodiment is a unique recording arrangement with bundles of six to ten small (20–50 .mu.m in diameter), insulated, and flexible, noble metal wires that are arranged in a parallel or twisted array. The wire bundles are constructed so that each recording wire can collect multicellular signals from a small cluster of neurons, with tips that are incremental in length, so that many recording sites can be sampled along a single line of bundle insertion into the brain.

According to another embodiment, software routines, together with corresponding hardware, are used to perform specific signal correlation, adaptation, and distribution as part of a general recalibration procedure. A unique signal processing method is provided to convert recorded neural signals into a resultant signal that is useful for control of an external device. The present system incorporates neural net software routines to map actual neural signals onto desired movement functions with greater accuracy than ever possible before due to the preliminary determination of the dominant hemisphere of the subject so as to find the "real neurological address." This real neurological address or devoted neuronal aggregate is programmed into the device so as to compensate for the fact all executive functions and all volitional activities originate from the dominant hemisphere.

In accordance with an embodiment of the invention, a robot arm is controlled by the neural signals recorded directly from the voluntary movement (motor) control areas of the cerebral cortex of a subject. Note that in the present invention and methodology, many of the animal studies employing monkeys and other animals are not as useful since humans are different than other mammals when it comes to dominant hemisphere activity. That is, in monkeys, for example, generally 50% are left hemisphere dominant, while the other 50% are right hemisphere dominant. The dominant brain hemisphere of other animals is determined randomly and without result to activity or effect. However, as is well known, most humans are right handed (up to 90% or so). Thus, the control of robotics or prosthetics based on an initial determination of the handedness (i.e. the dominant hemisphere of the brain) will enormously effect the accuracy of the ultimate activity of the device being moved thereby, now that volitional control is understood to originate from the dominant hemisphere of a human being.

It can be appreciated, however, that the concepts and general procedures of using neural signals to control movements of a robot arm are valid for the control of any external device that can be manipulated directly or indirectly by electrical or other emitted signals and are not limited to use with humans.

In distinction to the methods described previously, however, the present method would include a compensation for hemispheric dominance based on applying a vectorial analysis comprising determining the handedness of the subject wherein crossed uncrossed differential (CUD), properly interpreted to account for negative values, translates to a finding that all voluntary movements originate from the left hemisphere in true right handers (and the other way around in real left handers). Negative CUD means that the subject's real neurological address is different from his adopted handedness. Correcting this mistake changes the negative into a positive value and makes the accuracy of replicating the individual's thought pattern much more reliable. Such a compensation was never employed in prior utilizations, and hence, the present method is more accurately represents true brain activity based on hemispheric dominance. In further accordance with the present invention, there is provided a medium comprising a recorded neuronal signal. Such a neuronal signal can be obtained by obtaining neuronal signals derived from a population of brain cells devoted to executive functions of a human subject and recording the thus obtained signal into a suitable recording medium.

In order to control robotics or prosthesis, according to the present invention, one would first configure a computer program algorithm, for example, by chronically implanting microwaves in a subject sought to be duplicated in terms of brain activity. The implanted microwires would preferably comprise microwire arrays and would be implanted in multiple cortical areas, i.e., the left dorsal premotor cortex, left primary motor cortex, left posterior parietal cortex, right PMd and MI and right PP cortex, for example. Cortical recordings would be made and the data would be accessed and transformed into computer readable code for programming into the desired end use such as robotics or prosthetics. Note that when the data is being assessed, the negative crossed uncrossed differential, will be compensated for by providing that all voluntary activity of a right hander is generated by an electrical wave in the left side of the brain, and vice versa for left handers. This information will be incorporated into the analysis of the data received from the cortical recordings so as to provide a more accurate depiction of how the brain in the particular subject being assessed functions in terms of voluntary movement. In addition, it would be possible to actually isolate neurons and create a semiconductor device using methods and apparatus of the present invention as described, for example, by Zeck et al., "Noninvasive Neoroelectronic Interfacing With Synaptically Connected Snail Neurons Immobilized on a Semiconductor Chip" Proc. Natl Acad Sci. Aug. 28, 2001, 98 (18) 10457–10462 (incorporated herein by reference in its entirety) wherein a hybrid circuit of a semiconductor chip and synaptically connected neurons are implemented and characterized. Individual nerve cells from a snail were immobilized on a silicon chip by microscopic picket fences of polyimide. The implementation of silicon-neuron-neuron-silicon circuit constitutes a mechanism for neurocomputation, neuronal signal processing, neuroprosthetics or the like and could be utilized in some embodiments of the present invention.

What are the assumptions/predictions of the vectorial view and do those predictions correspond the clinical and laboratory findings? First: The most fundamental assumption of the vectorial view is the existence of an executor who is located at one or the other hemispheres, depending on a person's real neurological identity (RNA). Second: Since all volitional activities begin from the DNA with the bulk of it located in the major hemisphere (usually the left) the left hand follows the lead of the right hand by an amount equal to the interhemispheric transfer time (IHTT). And since this allows for the right hand to volunteer first and do more of daily activities it becomes the preferred hand. Third: As the two DNA moieties are part and parcel of the same substrate, an involvement of the major moiety is associated with bilateral manifestation of the effect of that lesion while the involvement of the minor moiety, or the liaison between the two moieties, will manifest itself only at one side; i.e. contralaterally. Fourth: Given von Monakow's transhemispheric diaschisis and the facilitating nature of the neuronal connection between the moieties of the DNA, there should be circumstances in which manifestation of deafferentation of the minor hemisphere is seen ipsilateral to a lesion with or without the presence of an excitatory phenomenon on the opposite side of the body. Laboratory observations, i.e. anatomical and physiological underpinning of the observations are depicted in Tables 1–3.

The present method starts with utilizing the test set forth by the Poffenberger paradigm, which is well known in the art since 1912. The Pofferberger test involves bilateral simultaneous or unilateral key pressing/releasing or other manual exercises, measuring simple or choice (discriminative) reactions times, with a temporal resolution in milliseconds. Whereas the use of questionnaires in arbitrarily defining ones laterality has been questioned on several grounds (1) including the nonconformity of the results with performance tests. The use of some version of Poffenberger paradigm has given consistent results whenever, by good luck, it was done in a cohort of uniform handedness. The vectorial approach, according to the present invention, however, allows further refining of the procedure by deciphering the puzzle of negative crossed uncrossed differential (CUD), as follows: Contrary to the classical view that appendicular movements are handled by the opposite hemisphere, according to the present invention, all voluntary movements originate from the left hemisphere in true right handers (and the other way around in real left handers). Acknowledging the fact that there is no difference in signal detection between the two hemispheres, the temporal ranking order from signal to movement in the vectorial scheme is different from that in the classical scheme (there being only two categories instead of four, i.e. VF/rh, uncrossed, and VF/lh, crossed in a right hand). Thus the asymmetry of the CUD in favor of the right hand in right handers is due to the fact that the right hand is plunged into action faster than the left by an amount equal to IHTT and that the negative CUD of earlier studies (in some of which the proportion of technical left handers amounted to a third of the participants) was due to the experimenters ignorance of proper rank ordering of stimulus-response delay in each individual of their studied sample. Expressed differently, the shortest reaction time obtained in performing the test belongs to the anatomically dominant hand for the reason indicated above. With the bug of negative CUD removed, the road is now clear for a technical definition of handedness, allowing an automatic solution to the problem of nonconformity between a person's stated handedness and his/her real neurological address (RNA). Such cases, who reveal their real neurological identity by becoming crossed aphasics or crossed nonaphasic upon an insult to their dominant or nondominant hemisphere respectively, form a group which continue to puzzle the experts of higher cortical functions.

The vectorial view of the callosal traffic underlying lateralities of executive functions (speech and handedness) states that the said laterality is based on the directionality of neural traffic connecting the two moieties of an apportioned neuronal aggregate devoted to these functions. The hemisphere that houses the larger moiety becomes the dominant hemisphere for these deliberate functions, literally driving the minor moiety amalgamated within the motor apparatus of the minor hemisphere. It is asserted that the two moieties are part and parcel of the same neuronal aggregate devoted to executive functions and that the said anatomic arrangement is occasioned merely by the existence of a gap between them (i.e. callosum). The vectorial view recognizes the nature of such connection as excitatory, based on the evidence adduced later on. Thus it is the apportioning of the devoted neuronal aggregate (DNA) housed within the motor apparatus of each hemisphere that constitutes the anatomy of lateralities in speech and manual preference. The left hemisphere contains the major moiety of the devoted aggregate in the vast majority of the population, rendering most subjects right handed in dexterity and left hemispheric for speech. It follows that the inheritability of executive functions will depend on the apportioning of the devoted neuronal aggregate distributed between the two hemispheres. It follows, as well, that such functions suffer differently should a strategically located lesion befall on one or the other hemisphere, resulting in bilateral finding in those lesions affecting the major hemisphere as the latter drives its sister portion located in the other. Lesions affecting the minor hemisphere or the liaison between the two moieties will have a limited consequence, manifested contralaterally.

In accordance with the present invention, techniques as high-resolution electroencephalography and magnetoencephalography (EEG, MEG), functional magnetic resonance imaging (fMRI), transcranial magnetic stimulation (TMS), and positron emission tomography (PET) can be employed. There is now increasing evidence that the Penfield-Boldrey homunculus is but a caricature of an intricate systems which includes the "primary motor cortex" as just one of at least three sources of corticomotoneuronal fibers influencing anterior horn cells, the others being cingulate and supplementary motor areas. The issue of existence of an ipsilateral pathway from the motor cortex to the anterior horn is still being debated, but the existence of a functioning ipsilateral influence in childhood seems to have been established, which normally matures and becomes masked by age 10, and unmasked when damage occurs. The "primary motor cortex" (MI) is said to be comprised of 3 contiguous but distinct areas related to arm, leg and face. Some have ascribed a cognitive role to this area which previously was considered only as a final common pathway to spinal motor neurons (Sanes and Donoghue, p 406). The fact that subjects with congenital partial or complete absence of callosum display manual preference indicates that the callosum is not necessary for preferential use of a hand at an individual level but clearly it becomes so at the population level wherein (as reflected in the observations summarized in tables 1–3 and the physiological explication of them presented here) a dichotomy of right-handers and nonright handers occurs.

To this scheme must be added the following four items: First: The existence of multiple central pattern generators along the neuraxis modifying the rate of automatic repetitive movements, such as breathing or carefree walking, by volition.

Second: The distinction between volitional and automatic movements: Neurologists are familiar with this matter as they witness a speechless aphasic swearing off emotionally or an apraxic patient waving bye as the doctor leaves the room while he could not do the same on request or by imitating (De Renzi), attesting to the fact that two types of movements are under different controls.

Third: The role of practice: This is of critical importance as witnessed by recent physiological and behavioral studies and by the fact that a sizable segment of population (an estimated 16%, see below) goes through life with manifest handedness only to reveal their real neurological address (RNA; identity) after a lesion rendering them crossed aphasic or crossed nonaphasic. An estimate of prevalence of manifest laterality, based on constant conjunction (i.e. nondissociability) of speech and handedness, is ~14–16 percent with two third of them occurring in nonright handers. Although such estimates appear too high by previous standards they are much closer to the results of more recent investigations of this subject both in the laboratory and at the bedside.

Fourth: The representation of laterality in executive functions revealed in the occurrence of bilateral signs upon injury of the dominant hemisphere and the finding of unilateral sign contralateral to the (injured) minor hemisphere upon the loss of its connection to the dominant hemisphere, either as a result of a lesion (iatrogenic or natural) in the corpus callosum (Table 1) or when the same set of fibers arising from the dominant hemisphere and destined for the minor one is affected such that a homolateral paralysis occurs due to transynaptic deafferentation (diaschisis) of the minor hemisphere, giving rise to a left sided paralysis in a right handed person or the opposite in a real (as opposed to a manifest) left hander (tables 2,3). In occasion the diaschisis is functional and resolves spontaneously, specifically in subdural hematoma (table 1, Wolf's case) and in 5% of strokes involving the left hemisphere, manifesting as "crossed aphasia". According to the vectorial view it is this very subsystem of motor control that underlies the phenomenon of handedness, or cerebral dominance, in motor control.

Clinicians have encountered both of the above mentioned findings for more than a century but have mistakenly attributed them to an incidental mishap (see below), missing the opportunity of gaining an insight to the neural underpinning of bimanual coordination and handedness, as detailed here. In table 2, observations of Kernohan's patients show that it is the involvement of the dominant hemisphere that resulted in the homolateral syndrome he described. This finding by Kernohan was not due to the notching of the contralateral cerebral peduncle by the tentorial attachment, but rather, due to the involvement of the dominant hemisphere. One of Kernohan's patients with supratentorial lesion had no notching of the peduncle and that notching in his eries was by no means always associated with ipsilateral clinical signs (18 of 40 notches were symptomatic). Kernohan does not suggest that a notching of cerebral peduncle does not cause any symptoms. What is asserted is that for a weakness to occur, ipsilateral to a (dominant) hemispheric lesion notching is neither necessary nor sufficient, as a careful reading of Kernhan's own data will show. (It is useful to note that prior to the widespread acceptance of Kernohan's simplistic claim one finds many writers who regarded ipsilateral weakness of the nondominant side upon injury to the dominant hemisphere, especially in cases of subdurals hematomas, a "classical" finding (table 2, Ectors.). The present invention, therefore relates to recognizing a separate subsystem of fibers and taking this into account when determining whether a subject is left or right hemisphere dominant. Note that in Table 2, the majority of reported instances do not mention signs expected to occur contralateral to the lesion itself (table 2, Magnan). There are however, reports of such instances by respected observers who, as a result of involvement of both subsystems, found themselves "in the quandary whether to attack the lobe corresponding to the paretic limb or that corresponding to the attack of local spasm", with the unfortunate results when the wrong side was chosen for an operation. The same criticism applies to the tenacious attribution of left sided postcallosotomy findings (variously described as paralysis, weakness or apraxia) to the use of a retractor when performing the procedure. See Akelaitis's and Marchiafava-Bignami syndrome (Table 1), relating to traumatic and vascular lesions of the callosum, or when no refractor had been applied in performing the procedure. Yet, despite the fact that a number of observers have questioned the validity of the retractor effect in relation to the occurrence of weakness in the non-dominant hand in callosotomy patients, this attribution is still being discussed in neuropsychological literature.

The underlying mechanism for both sets of observation, i.e. the occurrence of weakness on the non-dominant side upon deafferentation of the minor hemisphere, either as a result of a lesion in the corpus callosum (natural or iatrogenic) or when an appropriately placed insult affects the same set of fibers in the dominant hemisphere causing ipsilateral weakness is von Monakow's of diaschisis. Neurologists are familiar with this phenomenon, sometimes referred to as action at a distance, acknowledging its role in such syndromes as Bruns frontal ataxia or in bilateral visual field defects seen in unilateral occipital lobe lesions.

To sum: As depicted in tables 1–3, there is substantial clinical evidence that the dominance of the left hemisphere in executive functions as seen in vast majority of the population is underpinned by a vectorially operating facilitatory influence of the dominant hemisphere on the non-dominant one, occasioned by the existence of an identifiable neuronal substrate devoted to such functions which is disproportionately housed within the motor apparatus of each hemisphere, as detailed above. All voluntary actions of a right-handed person begin from the activity of this separate system, most of it housed within the left hemisphere. All commands for moving the left hand, therefore, is initiated in the left hemisphere and passed on to the minor moiety in the right hemisphere via the callosum.

It is therefore clear that left hand should follow the lead of the right hand in all bilateral "simultaneous" activities by an amount equal to interhemispheric transfer time (IHTT), the time it takes for the facilitating impulses to get from the left hemisphere (major moiety) to the right, and that there should, therefore, be an asymmetry of crossed-uncrossed differential (CUD) in favor of the right hand in all experiments using Poffenberger paradigms, if these were conducted on truly right handed patients. The situation should be reverse in a truly left handed. The asymmetry of CUD, which is indicative of the existence of a leading hemisphere, is also seen in vocalizing, verbalizing and gaze. (As these areas are served by cranial nerves they are not the primary concern of this article even though the subject is very germane to the topic at hand and points to the likelihood of existence of a generic design for the totality of voluntary motor control in humans.)

Thus, the present invention provides a technical and operational definition of handedness inspired by the vectorial view, substantiated by observations summarized in tables 1–3, and by electrophysiological investigations mentioned above: It is the right hand (in the vast majority of people) that volunteers firsts (and the left acts in coordination with it when the need arises). Clearly the anatomy mandates an earlier activation of the right hand giving it an ever-renewed priority in gaining experience by practice, constantly maintaining the synaptic efficiency of its cortical representation. This differential timing of activation of upper extremities, in addition, allows the performance of any seemingly "simultaneous" bimanual activity in which the dominant hand must beforehand supply the needed power to be acted upon "instantaneously" by the nondominant hand; as it occurs in such activities as playing a violin or a plucked musical instrument (where absolute simultaneity of action is a nonstarter). By using the example of the bowing and fingering hands of a performing violinist, it is clear that those instances of delicate and demanding performance of equal elegance by both hands, made possible by practice, in which the issue of "dominance" has no real meaning, except in the sequential timing issue mentioned above. The saying "practice makes perfect" applies, therefore, equally to both hands in a wider scheme of things. Nonetheless, and according to the theory outlined here, the hand that goes into the action first will naturally get to do more of it, becoming the "preferred hand", as mandated by nature. The other hand is left to do the best it can under the circumstances (see below).

Canonical teaching stresses (correctly) that the visual cortex of each hemisphere registers activity occurring in the contralateral visual field. Prior teachings assert (incorrectly) that each hemisphere controls voluntary movements of the contralateral side; hence arises the concept of "direction of anatomical predictability" which designates left visual field-left hand (LVF/lh) stimulus-response sequence as uncrossed (fast) and LVF/rh as crossed (slow, i.e. requiring the transfer of signal from the right to left hemisphere). The corresponding mirror images to these events are designated right visual field-right hand (RVF/rh, uncrossed) and right visual field-left hand (RVF/lh, crossed). The crossed mode of response occur most effectively when a normal callosum exists; else they are severely prolonged).

Marzi's et al's 1991 meta-analysis of experiments employed the Poffenberger paradigm and measuring crossed-uncrossed differential (CUD) as a measure of IHTT. They found a CUD asymmetry of 3.3 milliseconds (ms) in favor of impulses from the left visual field to the right hand when compared to those from right visual field to the left hand. Given the fact that in subsequent investigation Marzi and others found no significant difference in detection of the signal by the visual cortex of the two hemispheres, it is clear that the above asymmetry is attributable to the step(s) occurring later in the paradigm. Such a conclusion has since been confirmed by other investigators including Savage et al, who simultaneously recorded visual evoked and manual simple reaction times. None of the above investigators, however, succeeded in offering a cohesive view as to the nature of the asymmetry they found and none of them related their finding (i.e. the asymmetry of the CUD and rank order of their subjects manual simple reaction times) to the handedness of their subjects, as revealed by the vectorial view espoused by the present invention, in which, based on the anatomy depicted in tables 1–3, the rank ordering of the delay for the crossed modes is entirely different from that depicted in canonical teaching. Here, all voluntary activities initiated from the dominant hemisphere. The correct temporal rank order, therefore, have 2 categories: VF/rh and VF/lh for uncrossed and crossed (respectively) in dextrals and VF/lh and VF/rh as uncrossed and crossed in sinistrals. Since by definition no voluntary action takes place without conscious awareness, there is no need to stipulate a temporal sequence for "stimulus detection". This may be the logic behind the fact that no visual field advantage in simple reaction time or stimulus detection has ever been established and explain the virtual similarity of manual and verbal IHTT obtained under such paradigms (~2.4 ms, for both verbal and manual responses).

It appears, therefore, that the asymmetry of CUD in favor of the dominant hand highlighted by Marzi el al is the inevitable result of the existence of a command center located within the major hemisphere driving the minor moiety amalgamated within the motor apparatus of the minor hemisphere via their callosal connection. This is precisely the case when sufficient care is taken to select a reasonably pure collection of right or left handers, resulting in a minimum reaction time for VF/rh and maximum for VF/lh in right handers, affecting the CUD appropriately. For example when Savage et al in an experiment on a group of left handers, changed their selection criteria from Dean's schedule to simply the hand used for writing, there followed a significant change in simple reaction time in favor of the left hand, making it consonant with the prediction of vectorial view. Removing impurities of handedness within a group of left-handers accomplished the same in another setting, in which a vocal as well as manual response was examined, with similar effect on the CUD.

In accordance with the present invention, the Poffenberger test can be conducted. "Negative CUD" as used in the Poffenberger implies a faster intra-hemispheric than inter-hemispheric conduction. Thus, previously, a negative CUD suggested either an impurity of handedness within the examined population group due to admixture of real and manifest (left or right) handers, or 2) confusion in rank ordering of pathway used in determining a particular subject's crossed and uncrossed differences; i.e. RVF/rh in a right hander ranks differently from the same in a left hander; same applies for LVF/lh in two subjects of different laterality in motor control. These two sources of error have the same physiological basis and the distinction referred to is procedural in nature. The rank ordering of stimulus-response when ascertaining one's handedness plays a critical role in accordance with the present method.

High resolution EEG confirms that negative CUD can be compensated for as described herein.

The fundamental contribution of vectorial view in the role of callosum in underpinning laterality of executive functions are four: 1) It elucidates the neural underpinning of handedness, si demonstrates the bimodal nature of executive laterality in primates, including humans and emphasizes the physiological role of practice in establishing one's handedness. 2) It restores the "constant conjunction" of laterality of speech and handedness which had been sacrificed at the altar of contralateral control of motor function because of ignorance of distinction between volitional and automatic movements. 3) Therefore, it demystifies occurrence of crossed aphasia and crossed nonaphasias. 4) It brings enlightenment to the subject of apraxia by declaring it a disorder of movement control due to the involvement of the neuronal aggregate devoted to executive functions, as detailed above.

TABLE 1 nondominant weakness in patients with right cerebral dominance

| Author | Patient | Handedness | Defect | Weakness | Mutism | Apraxia | Right Anomia | Bimanual interaction | Additional information |
|---|---|---|---|---|---|---|---|---|---|
| B. Censori Boll. Soc. It. Biol. Sper. 65, 53 (1989). | 1-IC | Left | Two stage callosotomy | Right hemiparesis | Yes; after sectioning of splenium | | Yes | Impaired | Findings most sever after the 2nd stage splenectomy in both cases. |
| | 2-GS | Left | Two stage callosotomy | Right hemiparesis | Yes; after sectioning of splenium | | Yes | Impaired | |
| B. Meyer Ann. Neurol. 43, 360 (1998). | Case # 5, page 364 | Left | Anterior trunk | Right hemiparesis | | | | Impaired | Vascular insult involving anterior trunk. |
| H. Tei. Eur. Neurol. 34, 168 (1994). | 52 years old, page 168, 169 | Left | Posterior callosum remained intact | Right leg weakness | | Right agraphia | Yes resolved | | As a child he learned to write and use chopsticks with right hand. |
| A. Rosa Arch. neurol. 48, 986 (1991). | 54 years old | Left | Entire callosum | Right apraxia | | Right agraphia, apraxia | Yes | Impaired | Marciafava Bignami; right alien hand |
| A. Akelaitis Arch. Neurol. Psychiatr. 47, 971 (1942). | Case FP, Page 977 | Left | Entire callosum except tip of splenium | Right hemiparesis | Normal | Normal | Normal | Normal | Operated via a left frontal flap. No right hemisphere retraction occurred |
| M. Lassonde Brain 109, 953 (1986). | Case 5, page 956 | Left | Total callosotomy | Right arm and hand; see text | | Right arm and hand | | Impaired | Marked right clumsiness, specially distal muscles |
| M. Serdaru Brain 111, 829 (1988). | Case 22, page 835 | Left | callosotomy | Right hemiplegia | Yes | | | | Marciafava Bignami and Wernicke Korsakoff |

TABLE 2

Ipsilateral hemiparesis with lesion affecting the dominant left hemisphere

| Author(s), sources | Number of Cases | Handedness, Stated or Presumed | Location of Lesion | Nature of Lesion and additional comments | Side of Paralysis |
|---|---|---|---|---|---|
| W. Cuatico et al. J. Neurosurg. Sci. 23, 81 (1979). | 1 | Right handed, stated | Left hemisphere | Aneurysm, anterior communicating | Left side |
| A. Donnet et al. Neurochirurgie 43, 319 (1997). | 1 | Right handed, stated | Left temporal | Meningioma | Left side |
| L. Ectors et al. Neurochirurgie 4, 388 (1959). | cases #1, #4 | Right handed, presumed | Left Posterior frontal | Meningioma | Left side |
| E. Flateau Rev. Neurol. 1, 23 (1924). | case # 5 | Right handed, presumed | Left frontal lobe | Tumor, radiated on the wrong side, died; no notching | Left side |
| R. Hanchey et al. J. Neurosurg. 45, 108 (1976). | 1 | Right handed, presumed | Left hemisphere | Interhemispheric invasive ependymoma | Left side |
| Y. Itoyama et al. J. Neurosurg. 82, 645 (1995). | 1 | Right handed, presumed | Left hemisphere | Chronic subdural hematoma | Left side, 2 years duration |
| J. Kernohan et al. Arch. Neurol. Psychiatr. 21, 274, (1929). | 1 | Right handed, presumed | Left frontal | Glioma - no notching of peduncle was present | Left side |
| J. Kernohan et al. See above and text | 4 | Right handed, presumed | Left hemisphere | 1 Subdural 2 Gliomas 1 Abscess | Left side |
| J. Le Beau et al. Sem Hop. 37, 1990 (1961). | 1 | Right handed, presumed | Left hemisphere | Temporal meningioma | Left side |
| Dr. Magnan Brain 1, 562 (1878). | 1 | Right handed, presumed | Left hemisphere | Tumor | Left side |
| H. Masuzawa et al. No Shinkei Geka 22, 833 (1994). | 1 | Right handed, presumed | Left frontal | Trauma | Left side |
| E. Peyser et al. Int. Surg. 45, 689 (1966). | 5 | 3 Right handed, stated 2 Right handed, presumed | Left hemisphere | 3 Meningiomas 1 Glioma 1 Subdural | Left side |
| J. Vaquero et al. J. Neurosurg. Sci. 32, 127 (1988). | 2, page 169 | Right handed, stated | Left temporal | 1 AVM, 1 meningioma; CT scan showed no notching in either | Left side |
| R. Wolf et al. Lancet 345, 259 (1995). | 1 | Right handed, presumed | Left calvarium | Frontal subdural hematoma, operated on the wrong side | Left side, fully resolved spontaneously |

TABLE 3

Ipsilateral hemiparesis with lesion affecting the dominant right hemisphere

| Author(s), sources | Number of Cases | Handedness, Stated or Presumed | Location of Lesion | Nature of Lesion and additional comments | Side of Paralysis |
|---|---|---|---|---|---|
| R. Bencheikh et al Sem Hop Paris 63, 3211 (1987). | 1 | (manifest) Right hander | Right hemisphere | Meningioma | Right side |
| S. Dell et al Arch. Neurol. 40, 274 (1983). | 1 | Left handed, stated | Right hemisphere | Subdural hematoma | Right side |
| L. Ectors et al Neurochirurgie 50, 388 (1959). | case # 2 | (manifest) Right hander | Right frontal tumor, right paresis | Meningioma | Right side |
| R. Spaziante et al Neurochirurgie 36, 30 (1993). | 1 | (manifest) Right hander | Right pterion meningioma | Ipsilaterality of symptoms caused 7 year delay in diagnosis | Right side |

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined bye the appended claims and their equivalents.

As used herein and in the following claims, articles such as "the", "a" and "an" can connote the singular or plural.

All documents referred to herein are specifically incorporated herein by reference in their entireties.

What is claimed is:

1. A method for determining the dominant hemisphere of a human subject comprising:

measuring brain signals of said subject utilizing a modified Poffenberger Paradigm of said subject to measure the reaction time and deduce handedness of the subject based on plotting impulses from each of the two hemispheres of the brain of said subject;

employing a vectorial view of the role of callosum in the underpinning lateralities of speech and handedness, by obtaining neuronal signals derived from a population of cells devoted to executive function, and categorizing said neuronal signals such that all signals associated with voluntary movements are mapped and said map is analyzed to determine which hemisphere dominates for said subject, whereby the opposite hemisphere of the true handedness of said subject.

2. A method for replicating or predicting voluntary movement of a subject comprising:

determining the dominant hemisphere of said subject by obtaining neuronal signals derived from a population of neuronal cells of said subject that are devoted to executive functions;

compensating for any negative CUD (crossed uncrossed differential) determined during said determination by recognizing that all voluntary movements originate from the hemisphere that is opposite of the true handedness of said subject;

utilizing brain impulses of said subject taking into account said compensation to replicate or predict movements of said subject.

3. A recorded neuronal signal obtained from a method according to claim 2.

4. A method for controlling a prosthesis or a robot comprising:

determining the domanant hemisphere of said subject by obtaining neuronal signals derived from a population of neuronal cells of said subject that are devoted to executive functions and categorizing said neuronal signals such that all signals associated with voluntary movements are mapped and said map is analyzed to determine which hemisphere dominates for said subject, whereby the opposite hemisphere of the true handedness of said subject is defined as corresponding to the dominant hemisphere of said subject;

compensating for any negative CUD (crosses uncrossed differential) determined during said determination by recognizing that all voluntary movements originate from the hemisphere that is opposite of the true handedness of said subject;

utilizing brain impulses of said subject taking into account said compensation to control movements of said prosthesis or said robot.

5. A robot for implementing a method according to claim 4.

6. A prosthesis for implementing a method according to claim 3.

7. A method for imitating the hand coordination of a human being such that neuronal signals from the brain of said human being are extracted while said human is imagining an activity, said method comprising positioning a signal detection device on said human being;

determining said human being's dominant hemisphere by analyzing neuronal signals devoted to executive functions received from said electrodes;

creating a map for imitating movement based on an artificial neural network created from said neuronal signals;

encoding said map to a series of action potentials into a force to be exerted by an actuator so that said imagined activity is accomplished by said actuator.

8. A method according to claim 7, wherein said actuator is used in connection with real time control of a robotic device.

9. A method according to claim 8, wherein said control is local.

10. A method according to claim 8, wherein said control is remotely conducted via the Internet.

11. A recorded neuronal signal obtained from a method according to claim 7.

12. A system for replicating or predicting voluntary movement of a subject comprising:

a means for determining the dominant hemisphere of said subject using a modified Poffenberger Paradigm that can compensate for any negative CUD (crossed uncrossed differential) determined during said determination by recognizing that all voluntary movements originate from the hemisphere that is opposite of the true handedness of said subject;

a means for analyzing and utilizing brain emissions of said subject to replicate or predict movements of said subject.

13. An algorithm encoded on a device used to control a robot or a prosthesis, said algorithm comprising:

analyzing neuronal signals received from electrodes associated with brain impulses generated by a human subject;

creating a map for imitating movement based on an artificial neural network created from said neuronal signals;

encoding said map to a series of action potentials into a force to be exerted by said robot or prosthesis.

* * * * *